US00PP17401P2

(12) United States Plant Patent
Lowe

(10) Patent No.: US PP17,401 P2
(45) Date of Patent: Feb. 6, 2007

(54) ***GERANIUM* PLANT NAMED 'SATEENE'**

(50) Latin Name: *Geranium cinereum*
Varietal Denomination: Sateene

(75) Inventor: Carl Marius Lowe, Newport (GB)

(73) Assignee: Future Plants Licentie B.V., Lisserbroek (NL)

( * ) Notice: Subject to any disclaimer, the term of this patent is extended or adjusted under 35 U.S.C. 154(b) by 35 days.

(21) Appl. No.: 11/151,913

(22) Filed: Jun. 14, 2005

(51) Int. Cl.
*A01H 5/00* (2006.01)

(52) U.S. Cl. ..... Plt./324
(58) Field of Classification Search ..... Plt./324
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Geranium* plant named 'Sateene', characterized by its upright, broadly spreading and compact plant habit; numerous red purple-colored flowers with dark purple venation; and long flowering period.

2 Drawing Sheets

Botanical designation: *Geranium cinereum.*
Cultivar denomination: 'Sateene'.

BACKGROUND OF THE INVENTION

The present Invention relates to a new and distinct cultivar of *Geranium* plant, botanically known as *Geranium cinereum,* and hereinafter referred to by the cultivar name Sateene.

The new *Geranium* originated from a chance cross-pollination in 1999 of an unnamed selection of *Geranium cinereum,* not patented, as the female, or seed, parent with an unknown selection of *Geranium cinereum* as the male, or pollen, parent. The new *Geranium* was discovered by the Inventor in 2000 in a controlled environment in Newport, Shropshire, United Kingdom. Plants of the new *Geranium* differ primarily from plants of the female parental selection in flower color.

Asexual reproduction of the new cultivar by divisions in Newport, Shropshire, United Kingdom since 2002, has shown that the unique features of this new *Geranium* are stable and reproduced true to type in successive generations.

SUMMARY OF THE INVENTION

Plants of the cultivar Sateene have not been observed under all possible environmental and cultural conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Sateene'. These characteristics in combination distinguish 'Sateene' as a new and distinct cultivar:

1. Upright, broadly spreading and compact plant habit.
2. Numerous red purple-colored flowers with dark purple venation.
3. Long flowering period.

Plants of the new *Geranium* can be compared to plants of the cultivar Carol, disclosed in U.S. Plant Pat. No. 14,124. In side-by-side comparisons conducted by the Inventor in Newport, Shropshire, United Kingdom, plants of the new

*Geranium* differed primarily from plants of the cultivar Carol in flower color as plants of the cultivar Carol had purple-colored flowers.

BRIEF DESCRIPTION OF THE PHOTOGRAPHS

The accompanying colored photographs illustrate the overall appearance of the new *Geranium,* showing the colors as true as it is reasonably possible to obtain in colored reproductions of this type. Colors in the photographs may differ slightly from the color values cited in the detailed botanical description which accurately describe the colors of the new *Geranium.*

The photograph on the first sheet comprises a side perspective view of a typical one-year old flowering plant of 'Sateene' grown in a container.

The photograph at the top of the second sheet is a close-up view of a typical open flower of 'Sateene'.

The photograph at the bottom of the second sheet is a close-up view of a typical leaf of 'Sateene'.

DETAILED BOTANICAL DESCRIPTION

In the following description, color references are made to The Royal Horticultural Society Colour Chart, 2001 Edition, except where general terms of ordinary dictionary significance are used. Plants used for the following description were about one year old and grown under outdoor field conditions which closely approximate commercial production conditions during the spring in Lisserbroek, The Netherlands. During the production of the plants, day temperatures ranged from 7 to 20° C. and night temperatures ranged from 1 to 10° C.

Botanical classification: *Geranium cinereum* cultivar Sateene.

Parentage:

*Female, or seed, parent.*—Unnamed *Geranium cinereum* selection, not patented.

*Male, or pollen, parent.*—Unknown *Geranium cinereum* selection, not patented.

Propagation:

*Type cutting.*—By cuttings.

*Time to initiate roots.*—About one month at 12° C.

*Root description.*—Fine, fibrous; orange brown in color.

*Rooting habit.*—Freely branching.

Plant description:

*Plant form and habit.*—Perennial flowering plant; upright to broadly spreading and mounded growth habit. Compact plant habit; broad inverted triangle. Moderately vigorous.

*Plant height.*—About 13.5 cm.

*Plant diameter.*—About 18 cm.

*Lateral branch description.*—Number per plant: About seven. Length: About 6 cm. Diameter: About 2 mm. Internode length: About 3 cm. Texture, upper and lower surfaces: Smooth, glabrous. Color: 144B.

*Foliage description.*—Arrangement: Basal rosette. Length: About 2.6 cm. Width: About 2.8 cm. Shape: Orbicular. Apex: Acute. Base: Hastate; overlapping. Margin: Palmately lobed; lobes crenate. Texture, upper surface: Sparsely pubescent. Texture, lower surface: Smooth. Venation pattern: Palmate. Petiole: Length: About 8.5 cm. Diameter: About 1 mm. Color: Developing foliage, upper surface: Between 141A and 143A. Developing foliage, lower surface: 138A. Fully expanded foliage, upper surface: 137A. Fully expanded foliage, lower surface: 138A to 138B. Venation, upper surface: 143A. Venation, lower surface: 138A to 138B. Petiole: 143A.

Flower description:

*Appearance.*—Single rounded cupped to almost flat flowers with five petals with usually two flowers per lateral branch. Flowers face upright to slightly outwardly.

*Quantity of flowers.*—About 100 flowers develop per plant.

*Natural flowering season.*—Long flowering period, early May to late August in the Netherlands; flowering continuous during this period. Flowers not persistent.

*Fragrance.*—None detected.

*Flower longevity.*—About one week.

*Flower size.*—Length: About 2.7 cm. Diameter: About 7 mm.

*Flower buds* (*about five days before opening*).—Length: About 8 mm. Diameter: About 5 mm. Shape: Elliptic to ovate. Color: 137A to 137B.

*Petals.*—Length: About 1.5 cm. Width: About 1 cm. Shape: Broadly obcordate. Apex: Retuse. Base: Attenuate. Margin: Entire. Texture, upper and lower surfaces: Mostly smooth; towards the base, densely pubescent. Color: When opening and fully opened, upper surface: N74B; venation, between N79C and N186D. When opening and fully opened, lower surface: N74B to N74C; venation, between N79C and N186D.

*Sepals.*—Quantity: Five. Length: About 8 mm. Width: About 4 mm. Calyx shape: Rotate, slightly cupped. Sepal shape: Ovate to elliptic; apex, aristate; base, cuneate; margin, entire. Texture, upper and lower surfaces: Smooth. Color, upper surface: 137B. Color, lower surface: 137A to 137B.

*Peduncle.*—Length: About 7.4 cm. Diameter: About 1 mm. Angle: Erect to about 10° from vertical. Strength: Moderately strong. Color: 144A.

*Reproductive organs.*—Stamens: Quantity: Ten. Filament length: About 4 mm. Filament color: N79B; towards the base, 145D. Anther shape: Oblong, dorsifixed. Anther length: About 1.8 mm. Anther width: About 1 mm. Anther color: Between N186A and 202A. Pollen amount: Scarce. Pollen color: 197A. Pistils: Quantity: One. Pistil length: About 6 mm. Style length: About 4.5 mm. Style color: 138B. Stigma color: N186C. Ovary color: 138B.

*Seed description.*—Seed development has not been observed.

Disease/pest resistance: Plants of the new *Geranium* have not been noted to be resistant to pathogens and pests common to *Geranium*.

Garden performance: Plants of the new *Geranium* have been observed to have good garden performance and to tolerate wind and rain. Plants of the new *Geranium* have been observed to be hardy to USDA Zone 5 and to tolerate temperatures to about 35° C.

It is claimed:

1. A new and distinct cultivar of *Geranium* plant named 'Sateene', as illustrated and described.

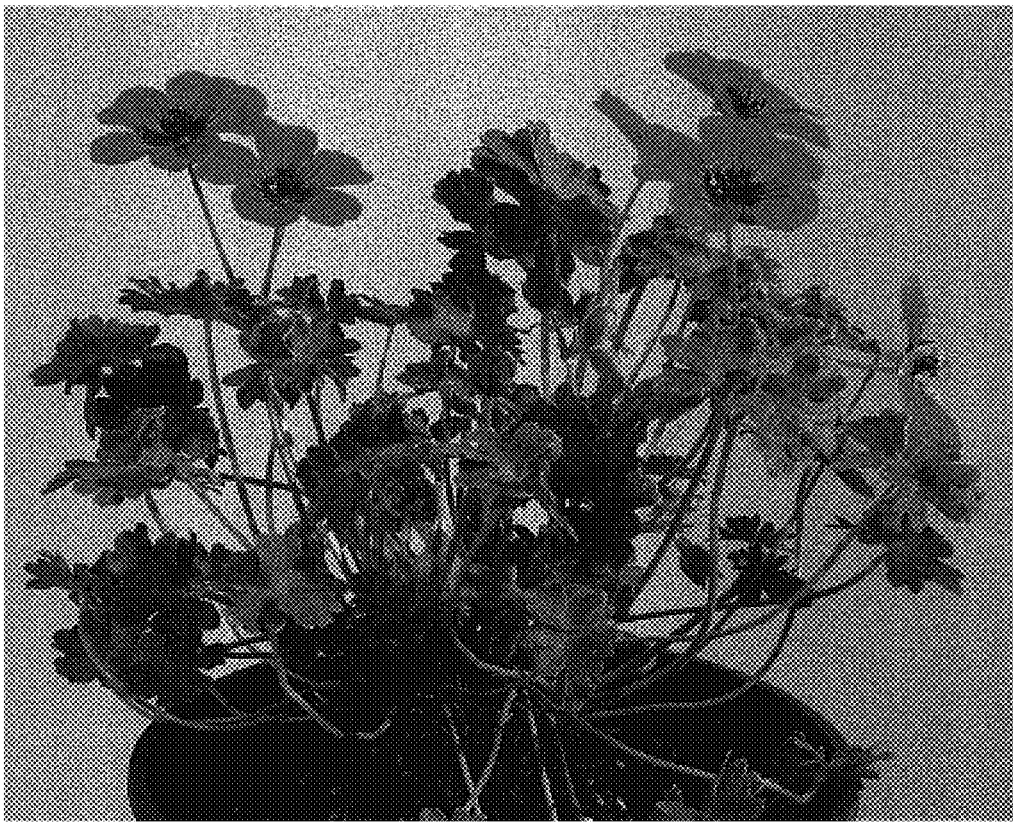

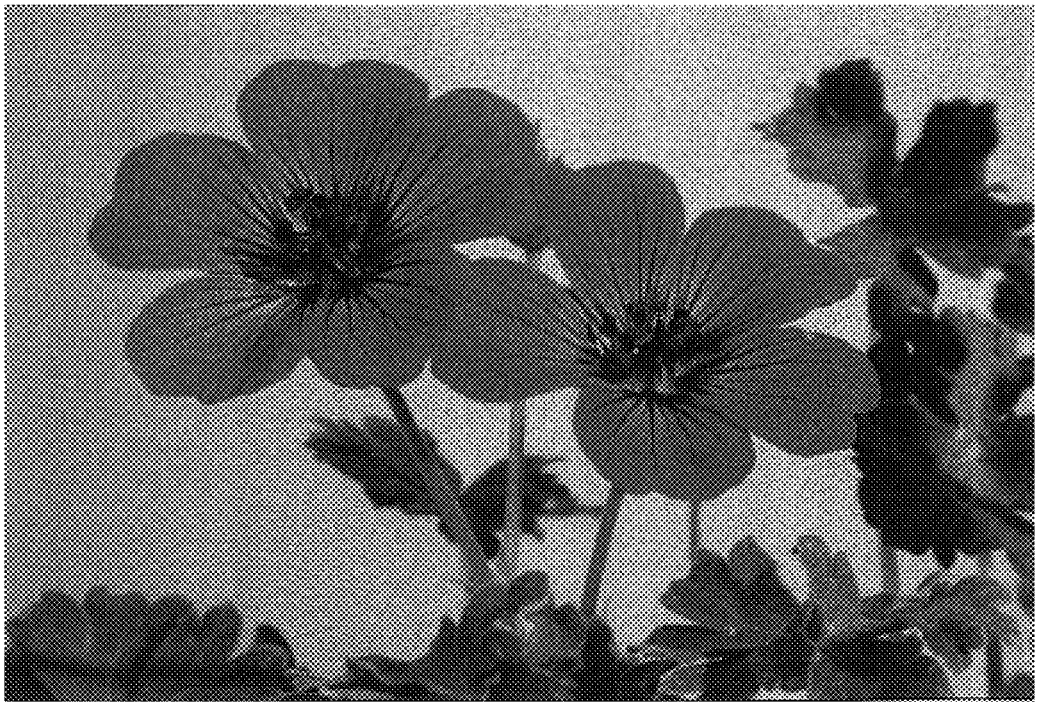
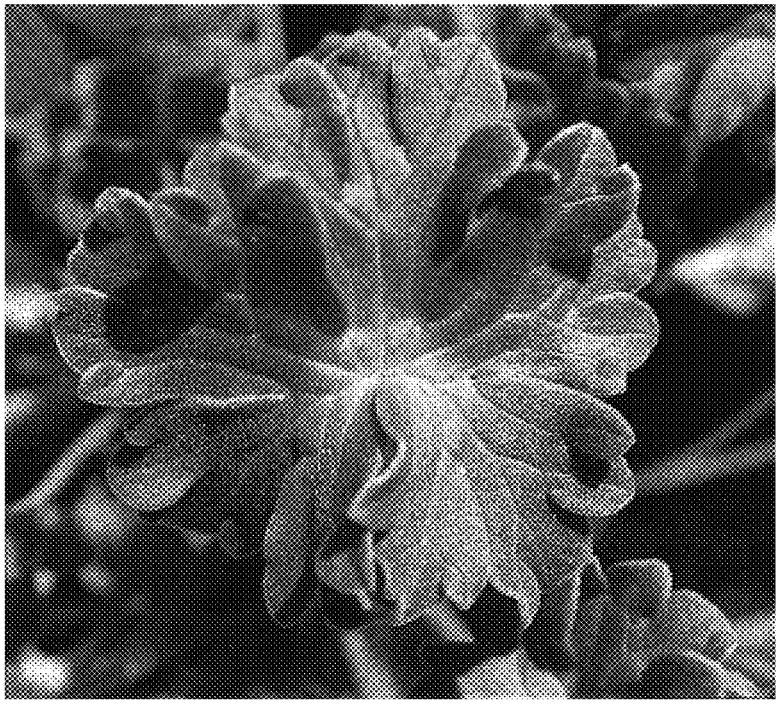

* * * * *